United States Patent

Sofranko et al.

Patent Number: 5,126,480
Date of Patent: Jun. 30, 1992

[54] ISOCYANATE PREPARATION

[75] Inventors: John A. Sofranko; Anne M. Gaffney, both of West Chester, Pa.

[73] Assignee: Arco Chemical Technology, L.P., Wilmington, Del.

[21] Appl. No.: 531,618

[22] Filed: Jun. 1, 1990

[51] Int. Cl.$^5$ .............................. C07C 263/00
[52] U.S. Cl. .................................... 560/338
[58] Field of Search .......................... 560/338

[56] References Cited

U.S. PATENT DOCUMENTS 4,207,251 6/1980 Heyboer .............................. 560/338

OTHER PUBLICATIONS

Mukaiyama et al. Chemical Comm. Jan. 1963 pp. 95-99.

Primary Examiner—Alan Siegel
Attorney, Agent, or Firm—William C. Long

[57] ABSTRACT

Isocyanates are prepared by catalytic cracking or pyrolysis of an amide according to the following reaction:

$$R(NH-\overset{O}{\underset{\|}{C}}-R_1)_x \longrightarrow R(NCO)_x + R_1H$$

wherein R is an alkyl or aryl group having 1 to 20 carbon atoms, $R_1$ is a lower alkyl group having 1 to 4 carbon atoms and x is a whole number from 1 to 3.

4 Claims, No Drawings

ISOCYANATE PREPARATION

BACKGROUND OF THE INVENTION

1. Field of the Invention

The present invention provides a method for the production of isocyanates. In particular, the invention provides a method for the production of an isocyanate, $R(NCO)_x$, by catalytically cracking at elevated temperature an amide having the formula

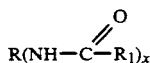

wherein R is an alkyl or aryl group having 1 to 20 carbon atoms, x is 1 to 3, and $R_1$ is an alkyl group having 1 to 4 carbon atoms.

2. Description of the Prior Art

Isocyanates are chemicals of great commercial importance, finding widespread use in the formation of urethanes and polyurethanes, for example. Procedures primarily used in the production of isocyanates involve the reaction of phosgene with the corresponding amine to form the isocyanate. Toluene diisocyanate which is widely used in the preparation of polyurethanes is made commercially by the reaction of toluene diamine with phosgene.

Because of the problems and expense associated with the use of phosgene, workers in this art have long sought alternative processes for isocyanate production. See, for example, such comprehensive reviews as "Syntheses and Preparative Applications of Isocyanates" by Reinhard Richter and Henri Alrich, Chapter 17, p. 619 of "The Chemistry of Cyanates and Their Thio Derivatives, Part 2," editor Saul Patai, published by John Wiley and Sons, 1977, New York, an Interscience Publication.

U.S. Pat. No. 3,314,754 shows the production of isocyanic acid by pyrolysis of alkyl carbamates.

Mukaiyama, et al. in Journal of the Chemical Society of Japan, Vol. 36, pages 95 through 99 (1963), showed the formation of small amounts of isocyanates by pyrolysis of phenylacetanilide.

Despite the efforts of prior workers to develop alternate routes to isocyanates, the phosgene process remains as the dominant commercial process.

BRIEF DESCRIPTION OF THE INVENTION

In accordance with the present invention, an improved process has been developed for the production of isocyanates which does not involve the use of phosgene. In essence, the process of the invention involves the catalytic cracking or pyrolysis of an amide to an isocyanate in accordance with the following equation:

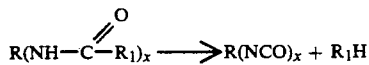

wherein R is an alkyl or aryl group having 1 to 20 carbon atoms, $R_1$ is a lower alkyl group having 1 to 4 carbon atoms, and x is a whole number from 1 to 3.

DETAILED DESCRIPTION

Amides which are converted to isocyanates by the process of this invention are those having the formula:

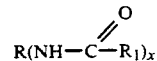

where R, $R_1$ and x have the values given above. Illustrative amides include acetanilide, toluyl diacetanilide, N-hexyl acetamide, N-cyclohexyl propanamide, N-amyl butyramide and the like.

The reaction is carried out in the liquid or vapor phase at 400 to 800° C., preferably 500 to 700° C. and at pressure ranging from 0 to 1000 psig. A solid catalyst is employed, and the feed can be diluted with inert gas such as nitrogen.

Catalysts which are employed are generally of the type known to activate the N-H bond. Illustrative classes of suitable catalysts are as follows:

1) Hydrogen Denitrogenation (HDN)-type Catalysts: Group VI Metals: Mo, W, Cr, in conjunction with Group VIII Metals Fe, Co, Ni, Ru, Rh, Pd, Os, Ir, Pt; as oxides and sulfides; supported on $S_iO_2$ and $AL_2O_3$.

2) Pd Black: This material is known to dehydrogenate amines to imines: *J. Am. Chem. Soc.* 95, 3038 (1973).

3) Supported Ag Catalyst: Can be prepared by chemical deposition of silver mirror on a carrier; this material has been used in the dehydrogenation of amines to nitrates: *Ind. Eng. Chem.*, 2046 (1948).

4) Basic Copper Compounds: Oxidative formation of benzonitrile from benzaldehyde with ammonia in a methanol solution has been catalyzed by some copper compounds such as cupric hydroxide, cuprous chloride and cupric chloride with sodium hydroxide or sodium metroxide—*Bull. Chem. Soc. Japn.* 4D, 912(1967); 41, 735(1968). Alkali metal promoted CuO, especially Na on CuO is especially useful.

5) Copper chromite-nickel catalysts: Primary amines undergo dehydrogenation on a copper chromite-nickel catalyst in the presence of $K_3PO_4$, and a mixture of products is formed, among them azomethine: *J. Org. Chem.*, 25, 2126 (1960).

6) Ni, Pt or Cr Catalysts: Catalytic dehydrogenation of secondary amines containing alpha hydrogens with Ni, Pt or Cr catalyst yields azomethines. U.S. Pat. No. 2,421,937 (1947).

7) $MnO_2$: Used to catalyze (6) above: *J. Org. Chem,* 29, 1540 (1964).

8) $FeCl_3$ or HgO: Oxidation of substituted hydrazine with $FeCl_3$ or HgO to hydrazones or azines: *J. Org. Chem,* 27, 3946 (1962).

9) Free Radicals such as RS.or $Cl_3C$.: Oxidation of azo compounds to azines by free radicals is known: *Rec. Trav. Chim.*, 74, 117 (1955).

10) Acids such as hydrochloric acid and sulfuric acid: Acid Catalyzed elimination of water from alpha-hydroxy secondary amine and elimination of an amine from a secondary 1,1-diamine to form imines is known: *J. Org. Chem,* 19, 1862 (1954). *J. Am. Chem Soc.*, 62, 1450 (1940).

11) $CS_2$ Used to catalyze acetone to ketene, a somewhat analagous reaction.

The following examples illustrate the invention:

EXAMPLE 1

To a quartz reactor was charged 0.5 g of 14-30 Mesh catalyst. Above the catalyst bed was charged 1.0 g of acetanilide. Nitrogen was passed through the tubular reactor at a rate of 10 cc/minute. The catalyst bed was heated to and equilibrated at 600° C. The solid acetamilide located directly above the catalyst bed was heated by another furnace from 100° C. to 200° C. during the run. The nitrogen flow forced the volatile acetanilide down through the catalyst bed. The gaseous reaction effluent was bubbled through an ethanol trap and then collected in a cumulative gas bag. Oil and solid residues collected below the catalyst bed during the run. After cooling the reactor to room temperature, this residue was recovered with an ethanol wash. The ethanol wash and trap solutions were analyzed by gas chromatography/mass spectrometry. Most of the reactant and products were found in the ethanol wash. Very little was found in the ethanol trap. The contents of the cumulative gas bag were analyzed by gas chromatography. From these analyses the % conversions and selectivities were determined. Mass balances ran 90% or better. For catalyzed runs selectivities to phenyl isocyanate were $\geq 58\%$. Under the trapping conditions used the phenyl isocyanate reacted with ethanol to give N-phenylurethane (reaction 1). Due to residual moisture in the ethanol, the phenyl isocyanate reacted with the water and subsequently decarboxylated to give aniline (reaction 2). The aniline further reacted with isocyanate to give carbonilide (reaction 3).

(Reaction 1)

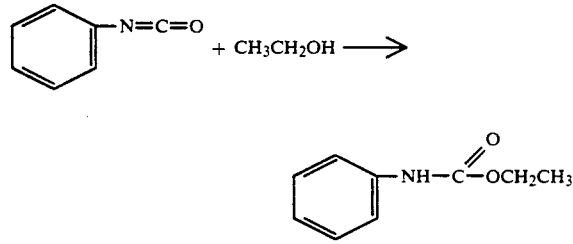

(Reaction 2)

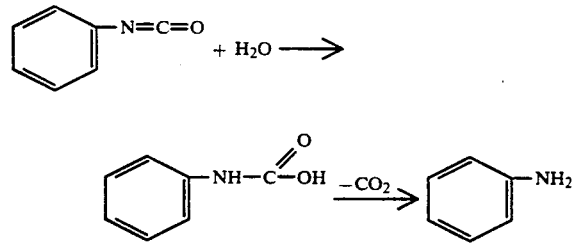

(Reaction 3)

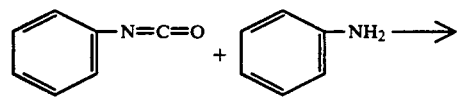

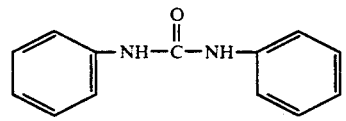

Thus, selectivities to phenyl isocyanate were based on the amounts of phenyl isocyanate, carbalide, N-phenylurethane and aniline found in the ethanol solutions. Non-selective products were benzonitrile, carbazole, indole and oxindole.

A control run was carried out in which no catalyst was charged to the reactor zone. The empty tubular section was heated to 600° C. and the solid acetanilide located directly above this vacant section was heated by another furnace from 100° C. to 200° C. during the run. Thermal conversion was only 1%. Note that the catalytic runs gave as high as 36% conversion.

The following table shows the results obtained:

TABLE 1

| Catalyst | Reaction Time | % Conversion | % Selectivity |
|---|---|---|---|
| 5% Na on CuO | 150 min. | 36% | 92% |
| 5% Pd on Carbon | 60 min. | 10% | 90% |
| Harshaw's HDN Catalyst of Nickel Molybdate | 60 min. | 10% | 78% |
| Harshaw's HDN Catalyst of Cobalt Molybdate | 60 min. | 6% | 95% |
| 15% Mo on SiO$_2$ | 60 min. | 4% | 58% |
| Control Run No Catalyst | 75 min. | 1% | 98% |

I claim:
1. The method for the preparation of an isocyanate having the formula R(NCO)$_x$ wherein R is an alkyl or aryl group having 1 to 20 carbon atoms and x is 1–3, which comprises catalytically cracking an amide having the formula

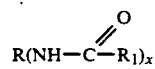

wherein R and x have the values given above and R$_1$ is an alkyl group having 1 to 4 carbon atoms in the presence of an N-H bond activating catalyst at elevated temperature in the range 400°–800° C. and at a pressure of 0–1000 psig to form said isocyanate and the lower alkane R$_1$H.

2. The method of claim 1 wherein said isocyanate has the formula R(NCO)$_2$ and said amide has the formula

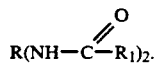

3. The method of claim 1 wherein the catalyst used comprises alkali metal on CuO.

4. The method of claim 1 wherein the catalyst used comprises Na on CuO.

* * * * *